US012324430B2

(12) United States Patent
Dyer et al.

(10) Patent No.: US 12,324,430 B2
(45) Date of Patent: **\*Jun. 10, 2025**

(54) TOPICAL ANTISEPTIC SYSTEM

(71) Applicant: INFECTION CONTAINMENT COMPANY, LLC, Bradenton, FL (US)

(72) Inventors: Dennie W. Dyer, Murrieta, CA (US); John A. Garruto, Encinitas, CA (US)

(73) Assignee: INFECTION CONTAINMENT COMPANY, LLC, Bradenton, FL (US)

( * ) Notice: Subject to any disclaimer, the term of this patent is extended or adjusted under 35 U.S.C. 154(b) by 31 days.

This patent is subject to a terminal disclaimer.

(21) Appl. No.: 17/583,964

(22) Filed: Jan. 25, 2022

(65) Prior Publication Data

US 2022/0142154 A1 May 12, 2022

Related U.S. Application Data

(60) Continuation of application No. 16/567,660, filed on Sep. 11, 2019, now Pat. No. 11,259,521, which is a division of application No. 15/189,709, filed on Jun. 22, 2016, now abandoned.

(60) Provisional application No. 62/327,736, filed on Apr. 26, 2016, provisional application No. 62/200,900, filed on Aug. 4, 2015, provisional application No. 62/183,059, filed on Jun. 22, 2015.

(51) Int. Cl.

| | |
|---|---|
| *A01N 25/24* | (2006.01) |
| *A01N 25/10* | (2006.01) |
| *A01N 33/12* | (2006.01) |
| *A01N 37/44* | (2006.01) |
| *A01N 59/12* | (2006.01) |
| *A01N 65/00* | (2009.01) |
| *A01N 65/08* | (2009.01) |
| *A61K 8/20* | (2006.01) |
| *A61K 8/41* | (2006.01) |
| *A61K 8/44* | (2006.01) |
| *A61K 8/73* | (2006.01) |
| *A61K 8/90* | (2006.01) |
| *A61K 9/00* | (2006.01) |
| *A61K 31/14* | (2006.01) |
| *A61K 31/198* | (2006.01) |
| *A61K 31/79* | (2006.01) |
| *A61K 33/18* | (2006.01) |
| *A61K 45/06* | (2006.01) |
| *A61K 47/10* | (2017.01) |
| *A61K 47/18* | (2017.01) |
| *A61Q 17/00* | (2006.01) |
| *A61K 47/34* | (2017.01) |
| *A61K 47/38* | (2006.01) |
| *A61K 47/44* | (2017.01) |

(52) U.S. Cl.
CPC ............. *A01N 25/24* (2013.01); *A01N 25/10* (2013.01); *A01N 33/12* (2013.01); *A01N 37/44* (2013.01); *A01N 59/12* (2013.01); *A01N 65/00* (2013.01); *A01N 65/08* (2013.01); *A61K 8/20* (2013.01); *A61K 8/416* (2013.01); *A61K 8/44* (2013.01); *A61K 8/731* (2013.01); *A61K 8/90* (2013.01); *A61K 9/0014* (2013.01); *A61K 9/0043* (2013.01); *A61K 31/14* (2013.01); *A61K 31/198* (2013.01); *A61K 31/79* (2013.01); *A61K 33/18* (2013.01); *A61K 45/06* (2013.01); *A61K 47/10* (2013.01); *A61K 47/183* (2013.01); *A61K 47/186* (2013.01); *A61Q 17/005* (2013.01); *A61K 47/34* (2013.01); *A61K 47/38* (2013.01); *A61K 47/44* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 4,206,204 | A | 6/1980 | Langford |
| 4,364,929 | A | 12/1982 | Sasmor et al. |
| 4,542,012 | A | 9/1985 | Dell |
| 4,671,957 | A | 6/1987 | Holtshousen |
| 4,849,215 | A | 7/1989 | Gottardi |
| 4,954,351 | A | 9/1990 | Sackler et al. |
| 5,071,648 | A | 12/1991 | Rosenblatt |
| 5,128,136 | A | 7/1992 | Bentley et al. |
| 5,137,718 | A | 8/1992 | Gillespie |
| 5,529,770 | A | 6/1996 | McKinzie et al. |
| 5,545,401 | A | 8/1996 | Shanbrom |
| 5,916,882 | A | 6/1999 | Jeng |
| 5,919,471 | A | 7/1999 | Saferstein et al. |

(Continued)

FOREIGN PATENT DOCUMENTS

| | | |
|---|---|---|
| CN | 103007365 A | 4/2013 |
| EP | 0284999 B1 | 12/1991 |

(Continued)

OTHER PUBLICATIONS

Elder et al. (Antimicrobial Preservatives Part Two: Choosing a Preservative). (Year: 2012).*

*Primary Examiner* — Tigabu Kassa
(74) *Attorney, Agent, or Firm* — Barnes & Thornburg LLP; Ryan L. Marshall

(57) ABSTRACT

Novel antimicrobial compositions and kits thereof containing these antimicrobial compositions, methods of manufacture and methods of use thereof are disclosed. The novel aqueous transdermal or topical delivery systems are useful, inter alia, for treatment of various microbial infections, including for use on tissue infections, particularly skin antisepsis and/or nasal mucosal tissue antisepsis to a mammalian host in need thereof.

17 Claims, No Drawings

(56) References Cited

U.S. PATENT DOCUMENTS

| | | | |
|---|---|---|---|
| 6,025,446 | A | 2/2000 | Kulkarni et al. |
| 6,696,041 | B2 | 2/2004 | Hansen |
| 6,846,846 | B2 | 1/2005 | Modak et al. |
| 6,927,197 | B1 | 8/2005 | Glick et al. |
| 7,014,871 | B1 | 3/2006 | Parsons et al. |
| 7,364,746 | B2 | 4/2008 | Hahn et al. |
| 7,659,344 | B2 | 2/2010 | Urian |
| 7,858,569 | B2 | 12/2010 | Glick et al. |
| 8,153,613 | B2 | 4/2012 | Ahmed et al. |
| 8,268,337 | B2 | 9/2012 | Wheeler |
| 8,303,994 | B2 | 11/2012 | Kessler et al. |
| 2003/0194415 | A1 | 10/2003 | Wang et al. |
| 2003/0228376 | A1 | 12/2003 | Mody et al. |
| 2006/0177511 | A1 | 8/2006 | Scholz et al. |
| 2007/0048338 | A1 | 3/2007 | Ladd |
| 2009/0226541 | A1 | 9/2009 | Scholz et al. |
| 2010/0183519 | A1 | 7/2010 | Katz et al. |
| 2011/0070316 | A1 | 3/2011 | Modak et al. |
| 2012/0294933 | A1 | 11/2012 | Reimer et al. |
| 2013/0121953 | A1 | 5/2013 | Lentini |
| 2014/0205559 | A1 | 7/2014 | Capriotti et al. |
| 2014/0219949 | A1 | 8/2014 | Liang et al. |
| 2014/0271529 | A1 | 9/2014 | Stogniew et al. |
| 2014/0322345 | A1 | 10/2014 | Liang et al. |
| 2014/0342024 | A1 | 11/2014 | Fusco |
| 2014/0343158 | A1 | 11/2014 | Fusco |

FOREIGN PATENT DOCUMENTS

| | | | |
|---|---|---|---|
| EP | 0639373 | B1 | 12/1998 |
| WO | 2000064255 | A1 | 11/2000 |
| WO | 2001010219 | A1 | 2/2001 |
| WO | 2004073683 | A1 | 9/2004 |
| WO | 2012007776 | A2 | 1/2012 |
| WO | WO 2012/002943 | * | 1/2012 |
| WO | 2013027065 | A1 | 2/2013 |

* cited by examiner

TOPICAL ANTISEPTIC SYSTEM

CROSS REFERENCE TO RELATED APPLICATIONS

This application is a continuation of U.S. application Ser. No. 16/567,660, which is a divisional of U.S. application Ser. No. 15/189,709 which claims the benefit of U.S. Provisional Application Ser. No. 62/183,059, filed Jun. 22, 2015, 62/200,900, filed Aug. 4, 2015 and 62/327,736, filed Apr. 26, 2016, the disclosures of each of which are hereby incorporated herein by reference in their entireties.

FIELD OF THE INVENTION

The present invention relates to antiseptic compositions containing an antimicrobial agent. More particularly, this invention relates to antiseptic compositions comprising an antimicrobial agent and methods of their use, including transdermal or topical administration for treatment of various microbial infections, including tissue, particularly skin antisepsis and/or nasal mucosal tissue antisepsis.

BACKGROUND OF THE INVENTION

In order to reduce the risk of infection, doctors and/or hospital surgical teams typically prepare or disinfect the skin prior to any invasive procedure such as surgery, catheterization, or needle puncture. Two traits of any preferred antiseptics are rapid kill of microorganisms and an ability to employ the antiseptic on in-tact skin, wounds including, for example, lacerations, punctures and/or burns, and/or mucosal tissue (e.g. vaginal, oral, nasal, and ocular tissue).

While alcohol-based antiseptics on the market for, inter alia, pre-surgical and pre-catherization antisepsis are fast acting they are generally unsuitable in a variety of applications including treatment of mucosal tissue or wounds.

In numerous instances of products with fast acting antimicrobial activity, the products lack a sustained activity to guard against microbial recontamination. In attempts to overcome this shortcoming, some products have been designed to adhere to the skin or tissue by forming a film barrier to microbial re-population. Any additional efficacy provided by the film must be balanced by their post-surgical removal requirement, which add to material and procedural costs as well as time by health care professionals. These increased costs must be absorbed by the patient or health care provider.

In spite of recent advances in antiseptic compositions and their administration, there remains a need for compositions that result in rapid, effective, and/or sustained microbial kill. There is also a need for compositions that can be effectively utilized over a range of surfaces, including, for example, in-tact skin, wounds including, for example, lacerations, punctures and/or burns, and/or mucosal tissue (e.g. vaginal, oral, nasal, and ocular tissue). Improvements that would allow health care professionals to obtain faster, more effective or longer acting antiseptics that may be useful over a broader range of a patient's anatomical surfaces without further complicating patient preparation or adding higher cost to such preparations are desirable. There is also still a need for antimicrobial compositions having increased speed and/or length of bactericidal activity on skin or mucosal tissue in a product that is delivered out of an aqueous vehicle, that preferably substantially remains on the tissue where applied. The present invention is directed to these and other important ends

SUMMARY OF THE INVENTION

Accordingly, the present invention is directed, in part, to topical antimicrobial compositions comprising an antimicrobial agent; a thickening agent, and water.

Accordingly, the present invention is directed, in part, to topical antimicrobial compositions comprising first and second antimicrobial agents; a thickening agent, and water.

In other embodiments, the present invention is directed to topical antimicrobial compositions comprising:
 an antimicrobial agent selected from the group consisting of $I_2$, an iodophor, and a combination thereof, wherein the antimicrobial agent is present in an amount sufficient to provide an available iodine concentration of at least about 0.25 wt-% and not more than about 1.5 wt-%;
 a thickening agent; and
 water;
  wherein:
   said composition is substantially free of any hydroxycarboxylic acid buffer.

In yet other embodiments, the present invention is directed to topical antimicrobial compositions comprising:
 an antimicrobial agent selected from the group consisting of $I_2$, an iodophor, and a combination thereof, wherein the antimicrobial agent is present in an amount sufficient to provide an available iodine concentration of at least about 0.25 wt-% and not more than about 1.5 wt-%;
 a thickening agent; and
 water;
  wherein said composition is substantially free of any fragrance.

In still other embodiments, the present invention is directed to topical antimicrobial compositions comprising:
 an antimicrobial agent selected from the group consisting of $I_2$, an iodophor, and a combination thereof, wherein the antimicrobial agent is present in an amount sufficient to provide an available iodine concentration of at least about 0.25 wt-% and not more than about 1.5 wt-%;
 a thickening agent; and
 water;
  wherein:
   said composition is substantially free of any hydroxycarboxylic acid buffer; and
  said composition is substantially free of any fragrance.

In other embodiments, the present invention is directed to topical antimicrobial compositions comprising:
 a first antimicrobial agent selected from the group consisting of $I_2$, an iodophor, and a combination thereof, wherein the antimicrobial agent is present in an amount sufficient to provide an available iodine concentration of at least about 0.25 wt-% and not more than about 1.5 wt-%;
 a second antimicrobial agent;
 a thickening agent; and
 water;
  wherein:
   said composition is substantially free of any hydroxycarboxylic acid buffer; and
   said composition is substantially free of any fragrance.

In some embodiments, the present invention is directed to topical antimicrobial compositions comprising:
 a first antimicrobial agent selected from the group consisting of $I_2$, an iodophor, and a combination thereof, wherein the antimicrobial agent is present in an amount sufficient to provide an available iodine concentration of from about 0.25 wt-% or more to about 1.5 wt-% or less;
a second antimicrobial agent;
a thickening agent comprising a nonionic cellulose derivative or nonionic copolymer, or combination thereof; and
water;
wherein:
said composition is substantially free of any hydroxycarboxylic acid buffer; and
said composition is substantially free of any fragrance.

In certain embodiments, the present invention is directed to methods of disinfecting tissue comprising:
applying directly to tissue an antiseptic composition at use concentration, wherein the use concentration of the composition comprises:
an iodophor comprising a carrier selected from the group consisting of a polyvinylpyrrolidone, a copolymer of N-vinyl lactam, a polyether glycol, a polyvinyl alcohol, a polyacrylamide, a polysaccharide, and combinations thereof; wherein the iodophor is present in an amount sufficient to provide an available iodine concentration of at least 0.25 wt-%;
a thickening agent; and
water;
wherein:
said composition is substantially free of any hydroxycarboxylic acid buffer; and
said composition is substantially free of any fragrance; and
allowing the antiseptic composition to remain on the tissue.

In certain embodiments, the present invention is directed to methods of disinfecting tissue comprising:
applying directly to tissue an antiseptic composition at use concentration, wherein the use concentration of the composition comprises:
an iodophor comprising a carrier selected from the group consisting of a polyvinylpyrrolidone, a copolymer of N-vinyl lactam, a polyether glycol, a polyvinyl alcohol, a polyacrylamide, a polysaccharide, and combinations thereof; wherein the iodophor is present in an amount sufficient to provide an available iodine concentration of at least 0.25 wt-%;
a second antimicrobial agent;
a thickening agent; and
water;
wherein:
said composition is substantially free of any hydroxycarboxylic acid buffer; and
said composition is substantially free of any fragrance; and
allowing the antiseptic composition to remain on the tissue.

In some other embodiments, the present invention is directed to methods of making an antiseptic composition at use concentration, the method comprising combining components comprising:
an iodophor comprising a carrier selected from the group consisting of a polyvinylpyrrolidone, a copolymer of N-vinyl lactam, a polyether glycol, a polyvinyl alcohol, a polyacrylamide, a polysaccharide, and combinations thereof; wherein the iodophor is present in an amount sufficient to provide an available iodine concentration of at least 0.25 wt-%;
a thickening agent; and
water;
wherein:
said composition is substantially free of any hydroxycarboxylic acid buffer; and
said composition is substantially free of any fragrance;
for a time and under conditions effective to form the antiseptic composition at use concentration.

In some other embodiments, the present invention is directed to methods of making an antiseptic composition at use concentration, the method comprising combining components comprising:
an iodophor comprising a carrier selected from the group consisting of a polyvinylpyrrolidone, a copolymer of N-vinyl lactam, a polyether glycol, a polyvinyl alcohol, a polyacrylamide, a polysaccharide, and combinations thereof; wherein the iodophor is present in an amount sufficient to provide an available iodine concentration of at least 0.25 wt-%;
a second antimicrobial agent;
a thickening agent; and
water;
wherein:
said composition is substantially free of any hydroxycarboxylic acid buffer; and
said composition is substantially free of any fragrance;
for a time and under conditions effective to form the antiseptic composition at use concentration.

In some embodiments, the present invention is directed to methods of disinfecting skin of a subject comprising:
prior to an invasive procedure, applying directly to the skin of the subject an antiseptic composition at use concentration, wherein the use concentration of the composition comprises:
an antimicrobial agent selected from the group consisting of $I_2$, an iodophor, and a combination thereof;
a thickening agent; and
water;
wherein:
said composition is substantially free of any hydroxycarboxylic acid buffer; and
said composition is substantially free of any fragrance; and
allowing the antiseptic composition to remain on the skin during the invasive procedure.

In some embodiments, the present invention is directed to methods of disinfecting skin of a subject comprising:
prior to an invasive procedure, applying directly to the skin of the subject an antiseptic composition at use concentration, wherein the use concentration of the composition comprises:
a first antimicrobial agent selected from the group consisting of $I_2$, an iodophor, and a combination thereof;
a second antimicrobial agent;
a thickening agent; and
water;
wherein:
said composition is substantially free of any hydroxycarboxylic acid buffer; and
said composition is substantially free of any fragrance; and
allowing the antiseptic composition to remain on the skin during the invasive procedure.

In still other embodiments, the present invention is directed to of disinfecting mucosal tissue of a subject comprising:
applying directly to the mucosal tissue of the subject an antiseptic composition at use concentration, wherein the use concentration of the composition comprises:
an antimicrobial agent selected from the group consisting of $I_2$, an iodophor, and a combination thereof, wherein the antimicrobial agent is present in an amount sufficient to provide an available iodine concentration of from about 0.25 wt-% or more to about 1.5 wt-% or less;
a thickening agent; and
water;
wherein:
said composition is substantially free of any hydroxycarboxylic acid buffer; and
said composition is substantially free of any fragrance; and
allowing the antiseptic composition to remain on the mucosal tissue.

In still other embodiments, the present invention is directed to of disinfecting mucosal tissue of a subject comprising:
applying directly to the mucosal tissue of the subject an antiseptic composition at use concentration, wherein the use concentration of the composition comprises:
a first antimicrobial agent selected from the group consisting of $I_2$, an iodophor, and a combination thereof, wherein the antimicrobial agent is present in an amount sufficient to provide an available iodine concentration of from about 0.25 wt-% or more to about 1.5 wt-% or less;
a second antimicrobial agent;
a thickening agent; and
water;
wherein:
said composition is substantially free of any hydroxycarboxylic acid buffer; and
said composition is substantially free of any fragrance; and
allowing the antiseptic composition to remain on the mucosal tissue.

In certain other embodiments, the invention is directed to methods of decolonizing the nasal passages of a subject comprising applying directly to the nasal passages of the subject a topical antimicrobial composition comprising:
An antimicrobial agent selected from the group consisting of $I_2$, an iodophor, and a combination thereof, wherein the antimicrobial agent is present in an amount sufficient to provide an available iodine concentration of from about 0.25 wt-% or more to about 1.5 wt-% or less;
a thickening agent; and
water;
wherein:
said composition is substantially free of any hydroxycarboxylic acid buffer; and
said composition is substantially free of any fragrance.

In certain other embodiments, the invention is directed to methods of decolonizing the nasal passages of a subject comprising applying directly to the nasal passages of the subject a topical antimicrobial composition comprising:
a first antimicrobial agent selected from the group consisting of $I_2$, an iodophor, and a combination thereof, wherein the antimicrobial agent is present in an amount sufficient to provide an available iodine concentration of from about 0.25 wt-% or more to about 1.5 wt-% or less;
a second antimicrobial agent;
a thickening agent; and
water;
wherein:
said composition is substantially free of any hydroxycarboxylic acid buffer; and
said composition is substantially free of any fragrance.

In certain other embodiments, the invention is directed to methods of disinfecting the tissue of a subject, the method comprising:
applying a topical antimicrobial composition to the tissue of the subject, said antimicrobial composition comprising:
an antimicrobial agent selected from the group consisting of $I_2$, an iodophor, and a combination thereof, wherein the antimicrobial agent is present in an amount sufficient to provide an available iodine concentration of from about 0.25 wt-% or more to about 1.5 wt-% or less;
a thickening agent; and
water;
wherein:
said composition is substantially free of any hydroxycarboxylic acid buffer; and
said composition is substantially free of any fragrance.

In certain other embodiments, the invention is directed to methods of disinfecting the tissue of a subject, the method comprising:
applying a topical antimicrobial composition to the tissue of the subject, said antimicrobial composition comprising:
a first antimicrobial agent selected from the group consisting of $I_2$, an iodophor, and a combination thereof, wherein the antimicrobial agent is present in an amount sufficient to provide an available iodine concentration of from about 0.25 wt-% or more to about 1.5 wt-% or less;
a second antimicrobial agent;
a thickening agent; and
water;
wherein:
said composition is substantially free of any hydroxycarboxylic acid buffer; and
said composition is substantially free of any fragrance.

The foregoing and other objectives, features, and advantages of the invention will be more readily understood upon consideration of the following detailed description of the invention.

DETAILED DESCRIPTION OF ILLUSTRATIVE EMBODIMENTS

As employed above and throughout the disclosure of the present invention, the following terms, unless otherwise indicated, shall be understood to have the following meanings.

As used herein, the term "substantially free" refers to a small amount of a specific component that may be contained in the compositions of the present invention. With regard to hydroxycarboxylic acid buffer, the term "substantially free" refers to an amount of 15% or less by weight of the hydroxycarboxylic acid buffer based on the weight of the composition, preferably 10% or less, more preferably an 5% or less, still more preferably 2.5% or less, even more preferably 2% or less, yet more preferably 1.5% or less yet even more preferably 1% or less, with only a de minimis quantity by weight, if any, contained in the composition being even more preferred. In certain other embodiments, the compositions are substantially free of a fragrance. Regarding this fragrance, substantially fragrance free compositions contain 1% or less by weight of any compound or mixture of compounds added to the composition for the primary reason of aesthetically improving the odor characteristics of the composition. Preferably, these substantially fragrance free compositions contain 0.5% or less, more preferably, 0.3% based on the weight of the composition, preferably 0.2% or less, more preferably 0.1% or less, still more preferably 0.05% or less, yet more preferably 0.4% or less, even more preferably 0.25% or less, with only a de minimis quantity by weight, if any being even more preferred. With regard to polyolefin, the term "substantially free" refers to an amount of 5% or less by weight of the polyolefin based on the weight of the composition, preferably 2% or less, more preferably an 1% or less, still more preferably 0.5% or less, with only a de minimis quantity by weight, if any, contained in the composition being even more preferred. With regard to sorbitan polyethoxylate or derivative thereof, the term "substantially free" refers to an amount of 5% or less by weight of the sorbitan polyethoxylate or derivative thereof based on the weight of the composition, preferably 2% or less, more preferably an 1% or less, still more preferably 0.5% or less, with only a de minimis quantity by weight, if any, contained in the composition being even more preferred.

In any of these ranges, the modifier "about" may be employed to either slightly broaden or diminish the amount, as would be understood by one of ordinary skill in the art.

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein, the term "substantive" as it applies to an antimicrobial compositions means that when an antimicrobial composition is applied to human skin or tissue as a uniform wet film or coating, the composition remains substantially localized at the point of contact, even though it may be contacted by certain bodily fluids present in the environment where the composition is being applied, preferably substantially localized for at least 30 minutes, more preferably for at least 1 hour, with for at least 2 hours being even more preferred. By "substantially localized", it is meant that 80% or more of the composition by weight being applied remains in the region about where it was applied for the time indicated, preferably 90%, more preferably 95% by weight being localized in the region where the composition was applied.

As used herein, the term "use concentration" refers to the concentration of a composition actually applied to the skin or tissue.

As used herein, the term "commercially acceptable shelf life" refers to the ability of a commercial product comprising a composition of the present invention to remain stable to substantial degradation of active therapeutic agent for a period of at least about 3 months under typical shelf storage conditions (about 20° C.), preferably at least about 6 months, more preferably at least about 12 months. Compositions were typically exposed to room temperature conditions or alternatively to oven storage temperatures of 30° C. or 40° C. and samples routinely taken to ascertain a threshold level of stability for USP povidone over time.

As used herein, the term "stable" refers to an antiseptic composition that shows no signs of visible gross phase separation (precipitation, phase split, settling, etc.) after storage at 40° C. for 5 days (preferably 10 days, more preferably 20 days, and yet more preferably 30 days, still more preferably 50 days, yet more preferably 75 days and even more preferably 90 days.

As used herein, the term "gel" refers to a three dimensional hydrophyllic network having chemical or physical cross-links, said networks capable of imbibing large amounts of water or aqueous biological fluids. Gels, as defined herein, are hydrated and thus contain some amount of water incorporated within them. Non-limiting examples of the numerous macromolecules capable of gel formation include polysaccharides, such as for example, alginate, carrageenan, destran, gellan, gura gum, hyaluronic acid, pullulan, schleroglucan, xanthan, xyloglucan, pectins, chitosan, and the like. "Gel precursors" or "gelling agents" typically refer to the same macromolecules, albeit in the absence of water or prior to hydration. These gel precursors preferably form gels in the presence of water and either certain ions or a variation in the pH of the aqueous solution.

When used in conjunction with water contained within an aqueous liquid medium, the term "substantially all" means that more than about 50% by volume of the aqueous medium employed in the present methods is water, preferably more than about 60% by volume, more preferably more than about 75% by volume, even more preferably more than about 90% by volume, still more preferably more than about 95% by volume, and most preferably more than about 99% by volume of the aqueous medium is water.

As used herein, the term "aqueous medium" and "aqueous liquid medium" each refer to a liquid medium comprising a substantial amount of water on a per unit volume liquid medium basis. Preferably, the aqueous medium is substantially all water, as defined herein.

As defined herein, and according to the US Pharmacopeia (USP), the term "purified water" refers to water that has been produced through the methods of either reverse osmosis, deionization, distillation or other methods that meet USP standards to remove impurities.

Therapeutic agents should be understood to include the neutral forms of the drug and pharmaceutically acceptable forms thereof. "Pharmaceutically acceptable" refers to those compounds, materials, compositions, salts and/or dosage forms which, within the scope of sound medical judgment, are suitable for administration to patients without excessive toxicity, irritation, allergic response, or other problems or complications commensurate with a reasonable benefit/risk ratio. By "pharmaceutically acceptable forms" thereof is meant any pharmaceutically acceptable derivative or variation, including stereoisomers, stereoisomer mixtures, enantiomers, solvates, hydrates, isomorphs, polymorphs, pseudomorphs, salt forms and prodrugs. Preferably in some embodiments, the pharmaceutically acceptable forms include salt forms. In other preferable embodiments the pharmaceutically acceptable forms include, any stereoisomer or stereoisomeric mixture of the therapeutic agent.

As used herein, the terms "preservative system" or "preservatives" include all preservatives approved for use in food and beverage compositions including, without limitation, such known chemical preservatives as benzoates including sodium, calcium, and potassium benzoate, sorbates including sodium, calcium, and potassium sorbate, citrates including sodium citrate and potassium citrate, polyphosphates including sodium hexametaphosphate (SHMP), and mixtures thereof, and antioxidants such as ascorbic acid, EDTA, BHA, BHT, TBHQ, dehydroacetic acid, dimethyldicarbonate, ethoxyquin, heptylparaben, and combinations thereof. Preservatives can be used in amounts not exceeding mandated maximum levels.

The invention is directed to, inter alia, the surprising and unexpected discovery of new topical antimicrobial compositions that may be administered to a subject. The present invention generally relates to topical antimicrobial compositions that contain at least two antimicrobial agents. Surprisingly, the compositions of the present invention are gentle and thus useful on mucosal tissue as well as in-tact skin. Generally speaking, antimicrobial (or antiseptic) compositions are applied to the tissue, typically skin, and allowed to dry and remain in place for at least 2 minutes, and often for several hours to days. Significantly, many of the compositions of the present invention maintain very low bacterial counts on the tissue, typically skin, for long periods of time, e.g., often up to 6 hours, and even up to 24 hours.

Desirable antiseptic compositions are aqueous-based and have one or more of the following characteristics: relatively high levels of bacterial kill; good adhesion to the skin; are capable of releasing an antimicrobial agent over a period of time; are suitable for use on sensitive tissues such as mucosal tissue; and may be removed relatively easily, preferably without the need for organic solvent-based removers.

Preferred antiseptic compositions of the present invention possess two or more of the above-mentioned characteristics. Significantly, in some embodiments, they provide rapid microbial kill and they are suitable for use on sensitive tissues such as mucosal tissue, as well as being capable of releasing an antimicrobial agent over a period of time.

Furthermore, preferred compositions of the present invention are very stable and can survive prolonged exposure to elevated temperatures, e.g., for prolonged periods of time, e.g., for often greater than 7 days. Preferred embodiments show no visible changes at all, such as changes in color, turbidity, and the like. As a non-limiting example, some embodiments are stable for 3 months at 40° C., which is the equivalent of 2 years at USP controlled conditions. As defined herein, the term "USP controlled conditions" refers to a temperature maintained thermostatically that encompasses the usual and customary working environment of 20° to 25° (68° to 77° F.); that results in a mean kinetic temperature calculated to be not more than 25°; and that allows for excursions between 15° and 30° (59° and 86° F.) that are experienced in pharmacies, hospitals, and warehouses. Provided the mean kinetic temperature remains in the allowed range, transient spikes up to 40° are permitted as long as they do not exceed 24 hours. Spikes above 40° may be permitted if the manufacturer so instructs. Articles may be labeled for storage at "controlled room temperature" or at "up to 25°", or other wording based on the same mean kinetic temperature. The mean kinetic temperature is a calculated value that may be used as an isothermal storage temperature that simulates the nonisothermal effects of storage temperature variations.

Preferred compositions of the present invention are also generally substantive. More preferred compositions of the present invention are substantive while in moist environments, such as the vaginal vault and/or nasal mucosa and remain localized for longer periods of time than typical antiseptics.

Preferred compositions of the present invention also possess viscosities that ensure the formulations go on easily and yet preferably remain substantially localized at the point of application.

A particularly important property of the compositions of the present invention is the ability to reduce the bacterial load on tissue, particularly skin, i.e., to kill the natural skin flora, rapidly. Preferably, compositions of the present invention are capable of reducing normal skin flora by at least about 1 log (10-fold), more preferably by at least about 1.5 log, and most preferably by at least about 2 logs (100-fold), in 2 minutes on a dry human skin site (typically, skin on an abdomen or back) using ASTM testing method E1 173-93 and a 30-second scrub with gauze soaked in the composition using moderate pressure.

This surprising rapid and high antimicrobial activity is provided through the use of iodine or an iodophor as the active antimicrobial agent in combination with a thickening agent in water, wherein the composition is substantially free of a hydroxycarboxylic acid buffer and/or substantially free of any fragrance, preferably substantially free of a hydroxycarboxylic acid buffer and substantially free of any fragrance, and in certain embodiments, rapid and high antimicrobial activity is provided through such compositions which further a second antimicrobial agent.

The gels, ointments, lotions or creams of the invention may be applied topically to the skin or to the various mucous membranes of the body, including but not limited to those of the oral, nasal, vaginal or rectal cavities.

In certain embodiments, a synergism toward antimicrobial activity may occur as a function of the combination of antimicrobial agents employed in the composition.

In other embodiments of the present invention, the topical antimicrobial compositions comprise: a first antimicrobial agent selected from the group consisting of $I_2$, an iodophor, and a combination thereof, preferably wherein the antimicrobial agent is present in an amount sufficient to provide an available iodine concentration of from about 0.25 wt-% or more to about 1.5 wt-% or less; a second antimicrobial agent; a thickening agent; and water.

In some embodiments, the topical antimicrobial compositions comprise: first antimicrobial agent selected from the group consisting of $I_2$, an iodophor, and a combination thereof, preferably wherein the antimicrobial agent is present in an amount sufficient to provide an available iodine concentration of from about 0.25 wt-% or more to about 1.5 wt-% or less. Preferably, the antimicrobial agent is present in an amount sufficient to provide an available iodine concentration of from about 0.5 wt-% or more to about 1.5 wt-% or less, still more preferably of from about 0.6 wt-% or more to about 1.4 wt-% or less; yet more preferably of from about 0.7 wt-% or more to about 1.3 wt-% or less; even more preferably of from about 0.8 wt-% or more to about 1.2 wt-% or less; with from about 0.85 wt-% or more to about 1.2 wt-% or less.

In certain embodiments, the first antimicrobial agent comprises $I_2$. In other embodiments, the first antimicrobial agent comprises an iodophor. In yet other embodiments, the first antimicrobial agent comprises a combination of $I_2$ and an iodophor.

Due at least in part to the nature of aqueous iodine-containing solutions, other iodine-containing species may be present in addition to iodine. Such species include, for example, hypoiodous acid (HOI), iodide ($I^-$), triiodide ($I_3^-$), iodate ($IO_3^-$), and the like.

In commercially available iodine disinfectants, it is typically desirable to maintain the disinfectant at an acidic pH in order to prevent rapid reduction of iodine to iodide, and/or to maintain stability in the iodine solutions. For example, commercial skin preps containing iodine generally have pH values in the range of from about 1.5 to 6.5, preferably from 1.5 to about 5; more preferably from 1.5 to about 4.5, still more preferably, from 1.5 to about 4, with from 1.5 to about 3.5 being even more preferred.

While iodine is generally thought to be the active germicidal ingredient in these types of formulation, it has limited water solubility. Consequently, a significant amount of research has been carried out on ways to improve its water solubility or its stability in final compositions. This includes research directed to "iodophors," in which elemental iodine or triiodide complexes with certain carriers. These iodophors function to not only increase the iodine solubility but to reduce the level of free molecular iodine in solution and to provide a type of sustained release reservoir of elemental iodine. Iodophors are known using carriers of polymers such as polyvinylpyrrolidone, copolymers of N-vinyl lactams with other unsaturated monomers such as, but not limited to, acrylates and acrylamides, various polyether glycols including polyether-containing surfactants such as nonylphenolethoxylates and the like, polyvinyl alcohols, polycarboxylic acids such as polyacrylic acid, polyacrylamides, polysaccharides such as dextrose, and the like In some instances a combination of two or more of these can be employed to complex the iodine. A preferred group of iodophors include polymers such as a polyvinylpyrrolidone (PVP), a copolymer of N-vinyl lactam, a polyether glycol (PEG), a polyvinyl alcohol, a polyacrylamide, a polysaccharide, and combinations thereof. Various combinations of iodophores can be used in the compositions of the present invention.

A preferred iodophor is povidone-iodine. A particularly preferred iodophor can be obtained commercially as povidone-iodine USP, which is a complex of K30 polyvinylpyrrolidone, iodine, and iodide wherein the available iodine (level of free $I_2$ plus iodine as complexed with the carrier) is present at about 9 weight % to about 12 weight % of the composition.

Preferably, the iodophor is present in the use compositions at a concentration of at least about 5 weight %, and more preferably at least about 7.5 weight %, and still more preferably greater than 9 weight %, based on the total weight of the antiseptic composition, with 10 weight % being even more preferred. Preferably, the iodophor is present in the use compositions at a concentration of at no more than about 16 weight %, and more preferably at no more than about 14 weight %, and still more preferably at no more than about 13 weight %, based on the total weight of the antiseptic composition, with at no more than about 12 weight % being even more preferred. In some alternatively preferred embodiments, iodophor, preferably iodine/povidone, it present in the use composition at a concentration of from about 9% to about 12% by weight, preferably from about 10% to about 12% by weight, with from about 10% to about 11% by weight of the composition being even more preferred. In alternative embodiments, the compositions of the present invention, are sufficient to provide an in use available iodine concentration of 85% to 120% of the labeled amount of iodine. In certain typical embodiments the label amount of Povidone-Iodine Solution will be, for example, 10% w/w (e.g., 1.0% available iodine USP).

Since iodophors may vary in the amount of available iodine, it is usually more convenient to describe the concentration in terms of the available iodine level. In the present invention, whether from iodine or an iodophor or a combination thereof, the available iodine concentration is preferably at least about 0.25 wt-%, and more preferably at least about 0.5 wt-%, based on the total weight of the antiseptic composition. The available iodine is preferably present at not more than about 1.5 wt-%, and preferably not more than about 1 wt-%, based on the total weight of the antiseptic composition.

The available iodine for most compositions may be determined by following the method in the United States Pharmacopeia Official Monograph for Povidone-Iodine, Assay for Available Iodine. Certain formulations may contain components that can interact with the method such as other anionic species. For this reason, the proper standards must be run to ensure accuracy, and solvent systems or reagents may need to be changed to ensure accuracy. One skilled in the art would appreciate these considerations.

In certain other embodiments, the compositions comprise a second antimicrobial agent. The second antimicrobial agent may be cationic or neutral. Exemplary neutral agents include ureas such as diazolidinyl urea, or isothiazolinones, such as methylchloroisothiazolinone and methylisothiazolinone, as well as other neutral agents known to those of skill in the art. Alternatively, or in combination therewith, the composition may comprise neutral antimicrobial agent EDTA as well as any salts thereof, such as its disodium salt. By way of example, the EDTA or salt thereof, preferably EDTA disodium salt, is present in the composition in the range of from about 0.005% to about 0.3% by weight, preferably from about 0.05% to about 0.3% by weight, more preferably from about 0.1% to about 0.3% by weight.

Exemplary cationic antimicrobial agents comprise benzalkonium salts such as the chloride salt. Additional cationic antimicrobial agents are exemplified by quaternary ammonium compounds ("QAC"). Quaternary ammonium compounds are a group of ammonium salts in which organic radicals have been substituted for all four hydrogens of the original ammonium cation. They have a central nitrogen atom which is joined to four organic radicals and one acid radical. QACs have a tendency to distribute to the interface of two phases (liquid-liquid or solid-liquid) to introduce continuity between the two different phases. QACs are known to have potent antimicrobial activity, capable of disrupting bacterial cell processes. QACs have been used as antiseptics, disinfectants, preservatives, biocides, etc.

Accordingly, in certain embodiments, the present invention relates to compositions and methods for their use, wherein the antimicrobial activities of gels, creams, ointments, or lotions is enhanced by the inclusion of quaternary ammonium compounds with iodine, an iodophor, or a combination thereof.

Examples of quaternary ammonium compounds suitable for use in the instant invention include, but are not limited to, benzalkonium chloride ("BZK"), benzethonium chloride ("BZT"), other benzalkonium or benzethonium halides, including, but not limited to, benzalkonium or benzethonium bromide or fluoride, cetyl pyridinium chloride, alkylamidopropalkonium chloride, behenalkonium chloride, behentrimonium methosulphate, behenamidopropylethyldimonium ethosulphate, stearalkonium chloride, olealkonium chloride, cetrimonium chloride, dequalinium chloride, N-myristyl-N-methyl-morpholinium methyl sulfate, poly [N-[3-(dimethylammonio)propyl]-N'-[3-(ethyleneoxyethelenedimethylammo-inio)propyl]urea dichloride], alpha-4-[1-tris(2-hydroxyethyl)ammonium chloride-2-butenyl]-omega-tris(2-hydroxyethyl)ammonium chloride, poly [oxyethylene(dimethyliminio)ethylene(dimethyliminio)-ethylene dichloride]. Any of the above may be provided in the form of an alternative salt, so long as the salt is pharmaceutically acceptable for its intended use in the composition. By way of guidance the quaternary ammonium compound, preferably benzalkonium chloride, is present in the composition in the range of from about 0.005% to about 0.3% by weight, preferably from about 0.005% to about 0.03% by weight, more preferably from about 0.01% to about 0.03% by weight. Alternatively preferred levels of quaternary ammonium compound, preferably benzalkonium chloride, in the composition are in the range of from about from about 0.003% to about 0.03% by weight, preferably from about 0.005% to about 0.02% by weight, more preferably from about 0.005% to about 0.01% by weight.

The concentrations of quaternary ammonium compound may be between about 0.005 and 0.5 percent by weight based on the composition; preferably the quaternary ammonium compound is benzethonium chloride or benzalkonium chloride at a concentration between 0.005 and 0.1 percent, more preferably between 0.005 and 0.05, still more preferably between 0.005 and 0.03 percent.

In certain embodiments, a synergism toward antimicrobial activity may occur as a function of the combination of antimicrobial agents employed in the composition.

In certain embodiments, the compositions comprise a thickening agent. The thickening agent may be monomeric, oligomeric or polymeric in its nature, or any combination of monomeric, oligomeric or polymeric thickening agents thereof. Exemplary monomeric thickening agents include alcohols and esters, for example, fatty alcohols, esters of fatty alcohols, and fatty acid esters, any of which may be isolated from natural sources or synthetically derived. Fatty alcohols are exemplified by any $C_{12}$-$C_{24}$ straight chain or branched alcohol, or any combination of two or more $C_{12}$-$C_{24}$ straight chain or branched alcohols. By way of example, a fatty alcohol, preferably comprising cetyl alcohol or stearyl alcohol or combination thereof, may be present in the composition in the range of from about 0.05% to about 2% by weight, preferably from about 0.1% to about 1% by weight, more preferably from about 0.1% to about 0.5% by weight, with from about 0.1 to about 0.3% by weight being even more preferred. These fatty alcohols may be used alone or in conjunction with glyceryl esters of fatty acids or ethoxylated fatty acid esters, such as polyethylene glycol esters of fatty acids, or any combination thereof. Thickening agents may also be selected based on their hydrophilic-lipophilic balance. Typically, such thickening agents have emulsification or composition stiffening properties and will usually have and HLB value of from about 12 to about 16. These agents may assist in the formation of oil in water emulsions and provide certain desired viscosity properties to the final compositions. In some embodiments, the thickening agent comprises glyceryl esters, preferably glyceryl esters of fatty acids, such as glyceryl stearate. Additional examples of alcohol ethoxylates may be found in Kirk Othmer Encyclopedia of Chemical Technology, $3^{rd}$ Edition, Volume 22, pages 364 and 365. Numerous examples of other glyceryl esters of fatty acids may be found in Kirk Othmer Encyclopedia of Chemical Technology, 3rd Edition, Volume 22, pages 367 and 368. These esters may be used alone or in conjunction with ethoxylated fatty acid esters, such as polyethylene glycol esters of fatty acids. For example, in some embodiments, a mixture of glyceryl stearate and PEG-100 stearate is employed as a thickening agent in the composition. Various combinations (ratios) of these two agents may be used by one of ordinary skill in the art to appropriately thicken or stiffen the composition to assist in its localization once applied to tissue. In certain preferred embodiments, about 2 wt. parts of glyceryl stearate per wt. part of PEG-100 stearate provides satisfactory results when used at a combined weight level of from about 2% to about 12% by weight of the composition; preferably from about 3% to about 11% by weight; more preferably from about 4% to about 10% by weight; with from about 5% to about 10% by weight being even more preferred. Alternatively, polyethylene glycol esters of fatty acids may be used as thickening agents. In other alternative embodiments, the thickening agent comprises silica. Additional organic or inorganic thickening agents are known in the art.

In still other embodiments, the thickening agents comprise an anionic or non-ionic polymer or copolymer. In addition to their usefulness as thickeners, these anionic or non-ionic polymers or copolymers may also provide better substantivity. These features allow the compositions to be retained on the tissue even while being exposed to bodily fluids or sweat and the like, and yet, preferably, still be reasonably easily removed when desired with mild cleaning agents such as soap and water. Generally speaking, the anionic or non-ionic polymers or copolymers comprise hydrophilic and hydrophobic moieties. When more substantivity in the compositions of the present invention is desired, an anionic or non-ionic polymer or copolymer should be selected based on higher levels of hydrophobic moieties. When more fluidity is desired, the level of hydrophilic moieties should be increased relative to the hydrophobic moieties. Non-limiting examples generally include anionic or non-ionic acrylate copolymers or carbomers. In some embodiments preferred copolymer thickening agents comprise copolymers of ammonium acryloyldimethyltaurate and vinylpyrrolidone monomers, or copolymers of $C_1 0$-$C_{30}$ alkyl acrylate with monomers of acrylic acid or methacrylic acid or any combination thereof. Examples of some commercially available polymeric thickening agents include VersaBase® Gel (PCCA, 9901 South Wilcrest Drive Houston, TX 77099); Carbomer Gel (Letco Medical, 1316 Commerce Drive, NW Decatur, Alabama 35601); and Adaptaderm Gel (Freedom Pharmaceuticals, 801 W. New Orleans St., Broken Arrow, Oklahoma 74011). Other preferred anionic acrylate copolymers including copolymers of acrylic acid, acrylamide, sodium acrylate and sodium acryloyldimethyltaurate monomers, such as, for example, Polyacrylate-13 and the like. While such polymers may be used as thickening agents alone, they may also be used in combination other known thickening agents including polyisobutene and/or polysorbitan polyethoxylates and their fatty acid esters, such as for example, Polysorbate 20. One such advantageous combination of Polyacrylate-13, Polyisobutene, and Polysorbate 20, known under the trade name SEPIPLUS™ 400, is provided by Société d'Exploitation de Produits Pour les Industries Chimiques, Paris France. In other alternative embodiments, thickening agents comprise a non-ionic copolymer, such as for example, a poloxamer. Poloxamers are nonionic triblock copolymers composed of a central hydrophobic chain of polyoxypropylene (poly (propylene oxide)) flanked by two hydrophilic chains of polyoxyethylene (poly(ethylene oxide)) and have the general structure shown below wherein a=2-130 and b=15-67:

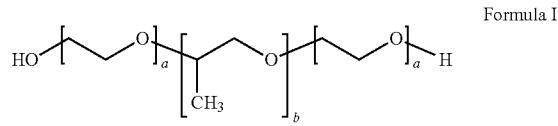

Formula I

Because the lengths of the polymer blocks can be customized, many different poloxamers exist that have slightly different properties, which are well understood to those of ordinary skill in the art. Once armed with the disclosures herein, any of a number of poloxamers may be chosen for use dependent at least in part on the properties desired in the final product. Because of their amphiphilic structure, the polymers have surfactant properties that make them useful in industrial applications. Among other things, they can be used to increase the water solubility of hydrophobic, oily substances or otherwise increase the miscibility of two substances with different hydrophobicities. Typically, the poloxamers of the present invention have the structure of Formula I wherein each a is independently in the range of from about 80 to about 120, preferably from about 90 to about 110, and b is in the range of from about 50 to about 80, preferably from about 55 to about 70. In other alternative embodiments, the typical the poloxamers have an approximate molecular mass of the poly(oxypropylene) core of 3500 to about 4500 g/mol and about 65 to about 75% of poly(oxyethylene) content by weight of the poloxamer. An exemplary poloxamer of this class for use in the compositions of the present invention is Poloxamer 407. Poloxamer 407 is a triblock copolymer which includes a central hydrophobic block of polypropylene glycol flanked by two hydrophilic blocks of polyethylene glycol. The approximate lengths of the two PEG blocks is 101 repeat units while the approximate length of the propylene glycol block is 56 repeat units. This particular compound is also known by the BASF trade name Pluronic F127 or by the Croda trade name Synperonic PE/F 127. In addition to viscosity modification properties, poloxamers, including Poloxamer 407, are known to incorporate into cellular membranes forming a biocompatible film. Without being held to theories of action, it is believed that formation of such a biocompatible film may allow the PVP/iodine element of the present invention to remain in contact with skin tissue such as that located in the interior of the nostril for extended periods of time. See Bartrakova E. V., "Pluronic Block Copolymers: Evolution of Drug Delivery Concept from Inert Nanocarriers to Biological Response Modifiers", *J. Control Release* 130, 98-106 (2008). By way of example, one or more poloxamers, such as for example Poloxamer 407, may be present in the composition in the range of from about 2% to about 15% by weight, preferably from about 5% to about 12% by weight, more preferably from about 6% to about 11% by weight, with from about 7% to about 10% by weight being even more preferred. These poloxamers may be used alone or in conjunction with one or more other viscosity modifiers (thickening agents), or any combination thereof.

Typically, anionic or non-ionic polymer or copolymer levels in antimicrobial compositions of the present invention are in the range of from about 0.1 to about 6% by weight of the composition, preferably from about 0.1 to about 5.5% by weight of the composition, still more preferably from about 2 to about 3% by weight of the composition. In combination-type polymer or co-polymer thickening agents, the relative ratio of the two or more components is not critical insofar as it does not interfere with the efficacy of the antimicrobial agent(s) and/or the substantivity on skin of the final composition. By way of guidance, a relative wt. ratio of Polyacrylate-13/Polyisobutene/Polysorbate 20 of from about 15:6:1 to about 10:5:1. In other embodiments, the relative wt. ratio of Polyacrylate-13 to Polyisobutene in the formulation is from about 3:1 to about 1:3, and all combinations and subcombinations thereof. In certain other embodiments, the relative wt. ratio of Polyacrylate-13 to Polysorbate 20 in the formulation is from about 5:1 to about 20:1, and all combinations and subcombinations thereof.

In yet other embodiments, the thickening agents comprise a modified cellulose derivative such as, for example, non-ionic soluble cellulose ethers. Hydroxyethyl cellulose is an exemplary compound in this family, and is soluble in both hot and cold water. Hydroxyethyl cellulose has good water retention and film formation. Owing to good thickening, suspending, dispersing, emulsifying, film-forming, water-protecting and protective colloid properties, hydroxyethyl cellulose has been shown to be useful in coatings, medicines, foods, and other fields. Modified cellulose derivatives such as, for example, non-ionic soluble cellulose ethers may be considered polymeric as well based on their backbone of repeating monosaccharides.

While such modified cellulose derivatives may be used as thickening agents alone, they may also be used in combination other known thickening agents, such as any families or individual thickening agents noted herein. By way of example, non-ionic soluble cellulose ethers, preferably comprising hydroxyethyl cellulose may be present in the composition in the range of from about 0.05% to about 5% by weight, preferably from about 0.1% to about 3% by weight, more preferably from about 0.1% to about 0.5% by weight, with from about 0.1 to about 0.3% by weight being even more preferred.

A suitable liquid vehicle for the antiseptic compositions of the present invention comprises water, to which acetone or an alcohol, particularly a ($C_1$-$C_4$) alcohol (i.e., a lower alcohol) such as ethanol, 2-propanol, and n-propanol, and mixtures thereof may be added. The use of alcohols in combination with water may enhance initial antimicrobial activity on tissue, or alternatively allow for reductions in surfactant levels. Preferably, the water is purified by any suitable means; more preferably the water or other vehicle is USP grade, including injectable-grade water, i.e., USP grade "water for injection."

Aqueous formulations (of the "non-lower alcohol" type) are typically preferred due at least in part to their gentleness to both skin and mucosal tissue.

In formulating compositions of this invention, it is contemplated that the formulations may further comprise ingredients which, while not having the activity of the above-named ingredients, will aid in the formulation and use of the composition as a whole. Examples of such ingredients are well-known to those of ordinary skill in the art of producing formulations for biological purposes. Examples of these ingredients include such substances as binders, emollients, humectants, preservatives (such as methyl paraben), lubricants, colorants, perfumes, and the like, such as those described in U.S. Pat. No. 5,951,993 (Scholz et al.), fragrances, colorants, tackifiers, plasticizers, etc. Accordingly, when the surface contemplated is skin, the composition of this invention may contain ingredients which are added to known lotions or medicaments, which are physiologically acceptable to skin and which do not contain ingredients which will reverse or retard the action of the irritant-inactivating agent. Surfactants may also be added to disperse the organic components or improve their solubility, inter alia, in the aqueous vehicle. In some embodiments, the compositions of the invention further comprise glycerin alone or in combination with allantoin. In certain alternative embodiments, the compositions of the invention further comprise a short chain ($C_1$-$C_4$) alcohol, a benzyl alcohol, an ethanol amine such as triethanol amine, or an emollient such as aloe, or any combination thereof.

In some embodiments, the compositions further comprise a surfactant. When the compositions include a surfactant, the surfactant may be anionic, cationic, amphoteric or non-ionic, or combination thereof. Alternatively, the surfactant is anionic or nonionic. In other embodiments that include a surfactant, it is nonionic. Surfactants may play any number of roles in the preparation and/or application of the compositions of the present invention, including, for example, improving the solubility or uniformity of dispersion for an iodophor in the aqueous composition. Alternatively or in combination, it may act to assist in reducing surface tension during application to mucosal tissue or skin tissue and/or facilitate drying of the composition on a tissue surface. They may also act to thicken the composition. Numerous examples of this class of molecules are known in the art. In certain embodiments, the surfactant acts to assist in emulsifying the more hydrophobic components in the aqueous composition. Preferably, the hydrophilic-lipophilic balance, as calculated by Griffin's method, is in the range of from about 8 to about 15, more preferably from about 8 to about 13, still more preferably from about 9 to about 12. Exemplary surfactants of this type include both anionic and non-ionic surfactants, preferably nonionics. Specific non-limiting examples of non-ionic surfactants of this type are fatty alcohol ethoxylates such as laureth 4. By way of example, the surfactant, preferably laureth-4, is present in the composition in the range of from about 2% to about 8% by weight, preferably from about 3% to about 7% by weight, more preferably from about 3% to about 6% by weight, with from about 3% to about 5% by weight of the composition being even more preferred. In alternative embodiments, the surfactant, preferably laureth-4, is present in the composition in the range of from about 1% to about 10% by weight, preferably from about 1% to about 7% by weight, more preferably from about 1% to about 6% by weight. Alternately preferred compositions contain non-ionic surfactants at levels in a range of from about 0.5% to about 7% by weight, preferably from about 1% to about 6% by weight, more preferably from about 1.5% to about 4% by weight, with from about 2% to about 3% by weight of the composition being even more preferred. Additional examples may be found in Kirk Othmer Encyclopedia of Chemical Technology, $3^{rd}$ Edition, Volume 22, pages 364 and 365.

In yet other embodiments, the compositions further comprise an emollient or moisturizer. Moisturizers or emollients are mixtures of chemical compounds specially designed to make the external layers of the skin (epidermis) softer and more pliable. They increase the skin's hydration (water content) by reducing evaporation. Naturally occurring skin lipids and sterols, as well as artificial or natural oils, humectants, emollients, lubricants, etc., may be part of the composition of commercial skin moisturizers. They usually are available as commercial products for cosmetic and therapeutic uses. Emollients can include, for example, fatty alcohols such as $C_{12}$ to $C_{20}$ fatty alcohols, naturally occurring oils such as jojoba oils or products derived from such oils and esters. In some embodiments, the moisturizers also assist in viscosity building or modifying. For example, International Flora Technologies, Ltd. Of Chandler, Arizona provides certain ester products, for example, Floraesters 20, Floraesters 30, and Floraesters 60, based on *Simmondsia chenensis*, that have this dual property capability. By way of example, jojoba esters, such as Floraesters 20, Floraesters K-20 W, Floraesters 30, and Floraesters 60, may be present in the compositions of the present invention in the range of from about 1% to about 8% by weight, preferably from about 2% to about 7% by weight, more preferably from about 2% to about 6% by weight. Alternatively preferred ranges for any of the Floraester products in compositions of the present invention range from about 0.1% to about 6% by weight, preferably from about 0.3% to about 6% by weight, more preferably from about 0.5% to about 6% by weight, still more preferably from about 0.5% to about 4% by weight, yet more preferably from about 0.5% to about 2% by weight. Other exemplary esters of fatty acids and fatty alcohols, saturated and/or unsaturated, from natural or synthetic sources, may be capable of providing one or both of these desirable properties.

Other exemplary emollients include but are not limited to Procetyl 10 PPG-10 cetyl ether, Procetyl 50 PPG-50 cetyl ether, Promyristyl PM-3 PPG-3Myristyl ether, PPG-3 benzyl ether myristate (Crodamol STS of Croda), PEG 20 Almond Glycerides, Probutyl DB-10, Glucam P20, Glucam E-10, Glucam P-10, Glucam E-20, Glucam P-20 distearate, glycerin, propylene glycol, cetyl acetate and acetylated lanolin alcohol (Acetulan), and hydroxylated milk glycerides.

In some other embodiments, the compositions further comprise glycerin, a glycerin ether compound, an ethoxylated glycerin compound, or a combination thereof. In embodiments where the compositions further comprise glycerin, a glycerin ether compound, an ethoxylated glycerin compound, or a combination thereof, the compound or combination it is typically present as a thickening agent.

In certain embodiments, it is desirable that the Brookfield viscosity of the compositions of the invention be in a range of from about 1000 cP to about 3500 cP when measured at 23° C. using a Brookfield RVT ROTOVISCO viscometer and the procedure preferably as described in the Examples Section. This ensures easy handling and application to the tissue, while ensuring that the composition remains localized on the tissue. In some embodiments, the Brookfield viscosity of the compositions as initially prepared is in a range of from about 1200 cP to about 3000 cP, preferably from about 1300 cP to about 2500, more preferably from about 1300 to about 2100 cP. These measurements are typically carried out at room temperature (23°±2° C.). The small samples may be run in a 13R chamber. Speed for rotating the spindle is selected so that the torque measured falls within a range of from about 40 to about 60% of maximum. To identify the appropriate spin speed multiple tests are typically run on the sample at different speeds until the desired torque is obtained. In some embodiments the measurement on the sample of the invention is taken employing a number 27 spindle. Alternative embodiments may employ either a number 14 or a number 21 spindle for measuring the viscosity. In other embodiments, the initial viscosity at or near the time the composition is prepared (for example within 24 hours, preferably within 12 hours) is in the range of from about 1000, preferably from about 1100, to about 1600, preferably about 1500 cP. It may also be useful for the composition's viscosity to equilibrate and/or build over a period of days or weeks. For example, the viscosity of a composition of the invention having an initial viscosity of about 1300 to 1400 cP may build over one or two weeks to a viscosity in the range of from about 1600 to 2200 cP, preferably 1700 to 2150 cP, still more preferably from about 1750 to about 2100 cP at equilibrium. While typical emulsion based formulations equilibrate in about 48 hours, slowing down this viscosity building process may have the advantage of making initial handling such as product filling easier before the final desired range for application is reached.

In certain other embodiments, preferably in embodiments employing nonionic cellulose derivative or nonionic copolymer thickening agents, it is desirable that the Brookfield viscosity of the compositions of the invention be in a range of from about 50 cP to about 500 cP, preferably from about 80 cP to about 300 cP when measured at 23° C. using a Brookfield RVT ROTOVISCO viscometer and the procedure preferably as described in the Examples Section. This ensures easy handling and application to the tissue, while ensuring that the composition remains localized on the tissue.

In yet other embodiments, the compositions are substantially free of any hydroxycarboxylic acid, or buffer thereof, or combination thereof, as defined herein. The term "hydroxycarboxylic acid" as used herein, refers to beta- and/or alpha-hydroxy carboxylic acids salts thereof, lactones thereof, and/or derivatives thereof. These may include mono-, di-, and tri-functional carboxylic acids. The hydroxyl acids may have 1 or 2 hydroxyl groups and/or 1 or 2 carboxylic acid groups. Exemplary hydroxyl acids include, but are not limited to, lactic acid, malic acid, citric acid, 2-hydroxybutanoic acid, 3-hydroxybutanoic acid, mandelic acid, gluconic acid, tartaric acid, salicylic acid, as well as derivatives thereof (e.g., compounds substituted with hydroxyls, phenyl groups, hydroxyphenyl groups, alkyl groups, halogens, as well as combinations thereof)). These acids may be in D, L, or DL form and may be present as free acid, lactone, or salts thereof. Other suitable HAs are described in U.S. Pat. No. 5,665,776 (Yu et al.). In certain embodiments, the compositions are substantially free of lactic and/or malic acid. In some other embodiments, the compositions are substantially free of a hydroxyl acid compound or buffer, wherein the formula of the hydroxyl acid is represented by the formula:

$$R^1(CR^2OH)_n(CH_2)_mCOOH$$

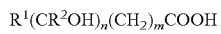

$R_1$ and $R_2$ are each independently H or a $(C_1-C_8)$alkyl group (saturated straight, branched, or cyclic group), a $(C_6-C_{12})$ aryl, or a $(C_6-C_{12})$ aralkyl or alkaryl group (saturated straight, branched, or cyclic alkyl group), wherein $R_1$ and $R_2$ may be optionally substituted with one or more carboxylic acid groups; m=0 or 1; and n=1-3, preferably, n=1-2.

In still other embodiments, the compositions are substantially free of any fragrance compound or essential oil, or menthol-based cooling agents.

In certain other embodiments, the compositions are substantially free of any cationic, film-forming polymer. In other embodiments, the compositions are substantially free of substantive film-forming polymers.

In certain other embodiments, the compositions are substantially free of any antimicrobial agent or preservative selected from the group consisting of chlorhexidine salts such as chlorhexidine gluconate (CHG), parachlorometaxylenol (PCMX), triclosan, hexachlorophene, fatty acid monoesters of glycerin and propylene glycol such as glycerol monolaurate, glycerol monocaprylate, glycerol monocaprate, propylene glycol monolaurate, propylene glycol monocaprylate, propylene glycol moncaprate, phenols, surfactants and polymers that include a (C12 C22) hydrophobe and a quaternary ammonium group, polyquaternary amines such as polyhexamethylene biguanide, quaternary silanes, silver, silver salts such as silver chloride, silver oxide and silver sulfadiazine, methyl, ethyl, propyl and butyl parabens, octenidene, and the like, as well as combinations thereof.

In certain other embodiments, the compositions are substantially free of any amphoteric surfactant. In yet other embodiments, the compositions are substantially free of any cationic surfactant. In some other embodiments, the compositions are substantially free of any anionic surfactant.

In certain other embodiments, the compositions are substantially free of any amine oxide.

In certain other embodiments, the compositions are substantially free of any $C_1-C_4$ alcohol.

In some other embodiments, the compositions are substantially free of any monosaccharide.

In certain other embodiments, the compositions are substantially free of one or more zinc salts such as, for example, zinc acetate (molar solubility in water of 1.64 moles/1), zinc butyrate (molar solubility in water of 0.4 moles/1), zinc citrate (molar solubility in water of <0.1 moles/1), zinc gluconate (molar solubility in water of 0.28 moles/1), zinc glycerate (moderately water soluble), zinc glycolate (moderately water soluble), zinc formate (molar solubility in water of 0.33 moles/1), zinc lactate (molar solubility in water of 0.17 moles/1), zinc picolinate (moderately water soluble), zinc propionate (molar solubility in water of 1.51 moles/1), zinc salicylate (low water solubility), zinc tartrate (moderately water soluble) and zinc undecylenate (moderately water soluble).

In still other embodiments, the compositions are substantially free of two or more ingredients selected from the group consisting of: hydroxycarboxylic acid, or buffer thereof; fragrance; cationic, film-forming polymer; substantive film-forming polymer containing hydrophyllic and hydrophobic moieties (as those are defined in U.S. Pat. No. 7,147,873, amphoteric surfactant; cationic surfactant; anionic surfactant; amine oxide; and monosaccharide.

In yet other embodiments, the compositions are substantially free of any melt extrudable polymer as that term is defined in U.S. Pat. No. 7,659,344.

In certain other embodiments, the compositions are substantially free of DMDM hydantoin.

In still other embodiments, the compositions are substantially free of a moisturizing agent selected from aloe vera, lavender, and chamomile.

In some other embodiments, the compositions are substantially free of any cationic thickener, cationic emulsifier, or cationic conditioning agent, or combination thereof as these terms are defined in US Published Application 2014/0343158.

In certain other embodiments, the compositions are substantially free of liposomes. In other embodiments, the compositions are substantially free of sodium alginate or microcapsules of sodium alginate.

In still other embodiments, the compositions are substantially free of dimethyl sulfoxide.

In certain preferred embodiments, the topical antimicrobial compositions are provided in kit form.

Accordingly, is some embodiments, the invention is directed to kits, comprising:
  a. a container comprising a topical antimicrobial composition of the present invention as described hereinabove; and
  b. instructions for applying the topical antimicrobial composition.

In certain preferred embodiments, the topical antimicrobial composition in the kit container provides an individual dose of therapeutic agent.

In other preferred embodiments, the kit further comprises and antiseptic mouthwash, more preferably a chlorhexidine containing mouthwash. In embodiments where the kit contains a mouthwash, the antimicrobial composition and mouthwash are administered in conjunction with, in any administration order, preferably substantially at about the same time, in any order to provide combined action against *Staphylococcus aureus* organisms or colony(ies) present in nasal or oral passages of a person in need of substantially reducing or eliminating the incidence of the *Staphylococcus aureus* infection.

The compositions of the present invention or kits containing such compositions are preferably supplied in the concentration intended for use but may be prepared as concentrates that are diluted prior to use. For example, concentrates requiring dilution ratios of 0.5:1 to 2.5:1 parts water to concentrate are contemplated. The higher limit of the concentrate is limited by the solubility and compatibility of the various components at higher concentrations.

The compositions of the present invention may be applied to the skin using any suitable means. Ordinarily an absorbent of some type such as gauze, foam sponges, non-woven fabrics, cotton fabrics, cotton swabs or balls, and the like, are soaked with the composition which is used to wipe the composition over the intended site. With very high activity compositions having exceptional wetting properties (e.g., higher alcohol content formulations), a single stroke prep may be all that is necessary. In most cases, however, it is believed that it helps to wipe the soaked absorbent across the skin several times, preferably in various directions, in order to thoroughly wet the skin and ensure good coverage into the finer details of the skin.

Pharmaceutical kits useful in, for example, the treatment of various microbial infections and or recolonization of microbials post initial treatment, as disclosed herein, which comprise a therapeutically effective amount of a first antimicrobial agent and a second antimicrobial agent indicated for the treatment of various microbial infections in a topical antimicrobial composition of the present invention, in one or more sterile containers, are also within the ambit of the present invention. Sterilization of the container may be carried out using conventional sterilization methodology well known to those skilled in the art, including for example, gamma irradiation. The sterile containers of materials may comprise separate containers, or one or more multi-part containers, as exemplified by the UNIVIAL™ two-part container (available from Abbott Labs, Chicago, Illinois), as desired. Multiple doses of the topical antimicrobial composition of the present invention may be separately packaged in unit dosage form, or combined into a single package form. Instructions, either as inserts or as labels, indicating quantities of the components to be administered, guidelines for administration, and/or guidelines for mixing the components, may also be included in the kit. The kits of the present invention further optionally comprise sterile applicators to apply the topical antimicrobial composition to the tissue or location desired for the treatment of any of a number of microbial infections, such as, Pro-Swabs™ (American Empire Manufacturing) or polyether or polyurethane sponges.

Methods Section

In other embodiments, the present invention provides processes for preparing the topical antimicrobial compositions of the invention described herein, comprising: combining components for a topical antimicrobial composition comprising:

an iodophor comprising a carrier selected from the group consisting of a polyvinylpyrrolidone, a copolymer of N-vinyl lactam, a polyether glycol, a polyvinyl alcohol, a polyacrylamide, a polysaccharide, and combinations thereof; wherein the iodophor is present in an amount sufficient to provide an available iodine concentration of at least 0.25 wt-%;

a second antimicrobial agent;
a thickening agent; and
water;
    wherein:
        said composition is substantially free of any hydroxycarboxylic acid buffer; and
        said composition is substantially free of any fragrance;
    for a time and under conditions effective to form the antiseptic composition at use concentration.

The topical antimicrobial compositions of the present invention may be prepared in any number of ways known to those skilled in the art. The components and final compositions can be synthesized, for example, by the methods described below, or variations thereon as appreciated by the skilled artisan. One or more of the components may be purchased from commercial suppliers. All processes disclosed in association with the present invention are contemplated to be practiced on any scale, including milligram, gram, multigram, kilogram, multikilogram or commercial industrial scale, topical antimicrobial compositions of the present invention, the order of addition of the first and second antimicrobial agents, the thickening agent, and water, as well as any surfactant, emulsifier, stiffener, emollient or other component for use in the topical antimicrobial composition is not critical. Thus, the first and second antimicrobial agents, the thickening agent, and water, as well as any surfactant, emulsifier, stiffener, emollient or other component for use in the topical antimicrobial composition may be contacted in an aqueous environment in any order. For simplicity, they may be added consecutively or simultaneously into the vessel used for their preparation. In some preferred embodiments it is advantageous to first contact the emollient, emulsifier and/or thickening agent in a first vessel for a time and under conditions sufficient to melt the components and provide a clear solution. In other preferred embodiments it is advantageous to first contact the second antimicrobial agent and water in a second vessel for a time and under conditions sufficient to dissolve the second antimicrobial agent in the water. In other preferred embodiments it is advantageous to contact the dissolved solution of second antimicrobial agent in the second vessel with surfactant and any first antimicrobial agent or further antimicrobial agent for a time and under conditions sufficient to prepare a homogeneous solution of the combined ingredients In still other preferred embodiments, it is advantageous to thereafter add the solution of the first vessel to the solution contained in the second vessel and to homogenize the mixture for a time and under conditions sufficient to homogenize the mixture. In yet other preferred embodiments, it is advantageous to thereafter with appropriate mixing to equilibrate the mixture, more preferably with removal of any excess heat that may have been added in a previous step. In some embodiments, one or more of the vessels is heated to facilitate mixing, dissolving, or homogenizing. When one of more of the vessels is heated, it may be heated to a temperature in the range of from about 30° C. to about 90° C., preferably from about 40° C. to about 85° C.; more preferably from about 50° C. to about 80° C.; still more preferably from about 60° C. to about 80° C.; with from about 68° C. to about 76° C. being even more preferred.

Topical antimicrobial compositions as described herein may be administered to a mammalian host, subject or "patient", such as a human host or patient, in a variety of ways adapted to the chosen route of topical administration.

Typically, antiseptic compositions are applied to the tissue, typically skin or mucosa, and allowed to dry and remain in place for at least 2 minutes, and often for several hours to days. Significantly, many of the compositions of the present invention maintain very low bacterial counts on the tissue, typically skin, for long periods of time, e.g., often up to 6 hours, and even up to 24 hours.

In other embodiments, the present invention provides methods of disinfecting tissue with a topical antimicrobial composition of the invention described herein, comprising:
  applying directly to tissue an antiseptic composition at use concentration, wherein the use concentration of the composition comprises:
    an iodophor comprising a carrier selected from the group consisting of a polyvinylpyrrolidone, a copolymer of N-vinyl lactam, a polyether glycol, a polyvinyl alcohol, a polyacrylamide, a polysaccharide, and combinations thereof; wherein the iodophor is present in an amount sufficient to provide an available iodine concentration of at least 0.25 wt-%;
    a second antimicrobial agent;
    a thickening agent; and
    water;
      wherein:
        said composition is substantially free of any hydroxycarboxylic acid buffer; and
        said composition is substantially free of any fragrance; and
  allowing the antiseptic composition to remain on the tissue; wherein the composition has a pH of 1.5 and 6.5.

In certain embodiments, the present invention provides methods of disinfecting skin of a subject with a topical antimicrobial composition of the invention described herein, comprising:
  prior to an invasive procedure, applying directly to the skin of the subject an antimicrobial composition at use concentration, wherein the use concentration of the composition comprises:
    a first antimicrobial agent selected from the group consisting of $I_2$, an iodophor, and a combination thereof;
    a second antimicrobial agent;
    a thickening agent; and
    water;
      wherein:
        said composition is substantially free of any hydroxycarboxylic acid buffer; and
        said composition is substantially free of any fragrance; and
  allowing the antiseptic composition to remain on the skin during the invasive procedure.

In yet other embodiments, the present invention provides methods of disinfecting mucosal tissue with a topical antimicrobial composition of the invention described herein, comprising:
  applying directly to the mucosal tissue of the subject an antiseptic composition at use concentration, wherein the use concentration of the composition comprises:
    a first antimicrobial agent selected from the group consisting of $I_2$, an iodophor, and a combination thereof, wherein the antimicrobial agent is present in an amount sufficient to provide an available iodine concentration of from about 0.25 wt-% or more to about 1.5 wt-% or less;
    a second antimicrobial agent;
    a thickening agent; and
    water;
      wherein:
        said composition is substantially free of any hydroxycarboxylic acid buffer; and
        said composition is substantially free of any fragrance; and
  allowing the antiseptic composition to remain on the mucosal tissue.

Various additional bacterial growth prevention, amelioration, or disinfection methods that substantially eliminate colonization by bacteria, such as *Staphylococcus aureus* (preferably methicillin resistant strains, i.e, MRSA) or other resistant bacteria on skin or mucosal tissue in a patient in need of such treatment are reasonably understood by the ordinarily skilled artisan once equipped with the disclosures provided herein. Typically, these methods involve application directly to the skin or mucosal tissue without dilution of a composition of the present invention as disclosed herein.

In other embodiments, the present invention provides methods of decolonizing the nasal passages of a subject with a topical antimicrobial composition of the invention described herein, comprising applying the a topical antimicrobial composition to the nasal passages of the subject.

The dosage of the first and second antimicrobial agents that comprise the water topical antimicrobial compositions or kits, may vary depending upon various factors such as, for example, the pharmacodynamic characteristics of the particular agent and its topical mode and route of administration, the age, health and weight of the recipient, the nature and extent of the bacterial contamination, the kind of concurrent treatment, the frequency of treatment, and the effect desired. Generally, a sufficient dosage may be transferred to the site of application with an applicator swab or sponge applicator that is sized to deliver an appropriate amount of the composition in view of the area of tissue to which the composition is to be applied. If necessary, the amount may be increased by small increments through the use of additional applications until the desired effect under the circumstances is reached.

It will be further appreciated that the amount of the topical antimicrobial composition required for use in treatment will vary not only with the particular agent or salt thereof selected but also with the area of tissue being treated, the applicator being employed, the nature of the condition being treated and the age and condition of the patient and will be ultimately at the discretion of the attendant physician or clinician.

The desired dose may conveniently be presented in a single dose or with subsequent dosage follow-up to appropriately cover the tissue being treated.

The disclosures of each of the foregoing documents are hereby incorporated herein by reference, in their entireties.

The invention provides for methods of using the foregoing compositions to achieve an antimicrobial effect comprising applying an effective amount of the composition to the skin or tissue. An antimicrobial effect significantly diminishes the risk of infection or progression of existing infection by one or more pathogenic infectious agent. The risk of infection need not be reduced to zero, but preferably is reduced by at least 10, 20, 30, 40, 50, 60, 70, 80, 90, 95 or even 99 percent. Examples of infectious agents against which protection may be afforded include, but are not limited to, *Staphylococcus* species such as *Staphylococcus aureus* and *Staphylococcus epidermidis, Streptococcus* species such as *Streptococcus pneumoniae, Enterococcus* species, *Salmonella* species such as *Salmonella typh, Escherichia* species such as *Escherichia coli, Vibrio species, Neisseria* species, such as *Neisseria meningitis* and *Neisseria gonorrhea*, Human Immunodeficiency Virus (HIV), Human Papilloma Virus (HPV), Herpes Simplex Virus (HSV), *Chlamydia trachomatis, Trichomonas vaginalis,* and *Candida albicans.*

The present invention is further described in the following examples. Excepted where specifically noted, the examples are actual examples. These examples are for illustrative purposes only, and are not to be construed as limiting the appended claims.

Experimental Section

The topical antimicrobial compositions are prepared in a lab-scale setting, utilizing common laboratory glassware and equipment. All chemicals and raw materials are purchased from certified suppliers such as Sigma-Aldrich, Fisher Scientific, Acros Organics, CP Kelco, and Gold Coast Ingredients. Materials: all chemicals were USP grade and used without further purification. Viscosity parameters: Spindle 27, Chamber 13R, Speed 60 rpm, Sample size 10.4 g, Run at room temperature (RT) for 2 minutes. Mixing and homogenizing are carried out on a Silverson L5M-A laboratory Mixer.

Accelerated Stability Test Procedures

A composition sample of known available iodine content is placed in an appropriately sized glass vial, which is in turn placed in a 40° C. oven. The sample is held at temperature for 3 months. Analysis of the sample after 3 months shows that the sample contains at least 85% of the available iodine contained initially in the sample.

Example A

Preparation of Topical Antimicrobial Composition

Step 1

In an appropriate size of beaker, combine jojoba esters (40 parts), cetyl alcohol (2 parts) and a mixture of 65% glyceryl stearate/35% PEG-100 stearate (80 parts). Heat the mixture to 72±3° C. until all ingredients are melted and a clear solution is obtained. Maintain the temperature at 72±3° C.

Step 2

In a manufacturing vessel, add purified water (qsad 1000 parts) and EDTA, disodium salt (2 parts). Heat the mixture to 72±3° C. with propeller mixing. Continue mixing until the EDTA disodium salt is completely dissolved. Maintain the temperature at 72±3° C.

Step 3

With mixing, add laureth –4 (40 parts), benzalkonium chloride (as a 50% aqueous solution) (2 parts) and PVP/Iodine (11 parts) to the manufacturing vessel. Continue mixing until the PVP-Iodine is dissolved and a homogeneous solution is obtained. Maintain the temperature at 72±3° C.

Step 4

Add the solution from Step 1 to the manufacturing vessel (Step 3) and homogenize the combined mixture until the mixture is uniform in composition (about 10 minutes).

Step 5

Switch to propeller mixing and initiate cooling to room temperature. Continue mixing until a smooth and homogeneous lotion is formed and the batch reaches room temperature.

The viscosity and pH of the final product are tested initially (1433 cP, pH is 3.36), after one week (2079 cP, pH is 2.93, and after two weeks (1804 cP, pH is 2.72).

The viscosity is evaluated in a Brookfield Viscometer, Model No. RVDVE 11S at room temperature (23° C.±2°) employing a number 27 spindle. The sample is evaluated at four different speeds (20, 50, 60, and 100 rpm) and viscosity and % torque are determined. The viscosity is determined initially (typically within 12 hours of the sample's preparation) and each week thereafter for three weeks. Any change in viscosity over time is noted. In some instances spindle 27 may be replaced by spindle 14 or by spindle 21.

Example B

Procedure:

Water (84.4 g) was placed in a sanitized mixing vessel. EDTA disodium salt (0.1 g) was added and dissolved into the water with continued mixing. Hydroxyelthylcellulose (HEC, 0.25 g) was slowly added with stirring to avoid clumping. NaOH (0.2 g of 20% by weight aqueous solution) was added and mixed until batch was completely smooth and free of "fish eyes". The remaining ingredients (Floraesters K=20 W jojoba (2.6 g), Laureth-4 (2 g), benzalkonium chloride (0.01 g), and sodium iodide (0.5 g) were independently added to ensure that each ingredient was dissolved before the addition of the next. PVP-iodine (9.726 g) was very slowly added to the mixture with mixing carried out as to avoid entrapment of air. PVP-I % was calculated according to "Available Iodine AS IS" assay found on COA (11.31%) for a total of 1.1% Iodine. The batch was mixed until batch was completely homogeneous.

APPEARANCE: Semi-viscous clear liquid
COLOR: Dark reddish/brown
ODOR: Characteristic-iodine
Initial pH @ 25° C.: 4.27
Initial VISCOSITY @ 25° C.: RVT: 280 cPs; Spindle 3, 50 RPM
MICROBIOLOGY: <10 CFU/gram, No pathogens The viscosity was evaluated in a Brookfield Viscometer, Model No. RVDVE 11S at room temperature (25° C.±2°) employing a number 3 spindle. The sample was evaluated at 50 rpm) and viscosity, pH and appearance were noted. The viscosity was determined initially (typically within 12 hours of the sample's preparation) and each week thereafter for 90 days. After 90 days, the viscosity was 266 cP and the pH was 3.29. No change in appearance was noticed.

Example C

Water (74.5 g) was placed in a sanitized mixing vessel. EDTA disodium salt (0.1 g) was added and dissolved into the water with continued mixing. Pluracare F 127 (analogous material to Poloxamer 407, 10 g) was slowly added to avoid introduction of excess air. PVP-iodine (9.73 g) was very slowly added to the mixture with mixing carried out as to avoid entrapment of air. PVP-I % was calculated according to "Available Iodine AS IS" assay found on COA (11.31%) for a total of 1.1% Iodine. NaOH (0.6 g of 20% by weight aqueous solution) was added and mixed until batch was completely smooth and free of "fish eyes". The remaining ingredients (Floraesters K=20 W jojoba (2.6 g), Laureth-4 (2 g), benzalkonium chloride (0.01 g), and sodium iodide (0.5 g) were independently added to ensure that each ingredient was dissolved before the addition of the next. The batch was mixed until batch was completely homogeneous.

APPEARANCE: Semi-viscous clear liquid
COLOR: Dark reddish/brown
ODOR: Characteristic-iodine
Initial pH @ 25° C.: 4.00-4.50
Initial VISCOSITY @ 25° C.: RVT: 102 cP; Spindle 3, 50 RPM
MICROBIOLOGY: <10 CFU/gram, No pathogens The viscosity was evaluated in a Brookfield Viscometer, Model No. RVDVE 11S at room temperature (25° C.±2°)

employing a number 3 spindle. The sample was evaluated at 50 rpm) and viscosity, pH and appearance were noted. The viscosity was determined initially (typically within 12 hours of the sample's preparation) and each week thereafter for 90 days. After 90 days, the viscosity was 102 cP at room temperature (25° C.±2°) employing a number 3 spindle. and the pH was 3.29. No change in appearance was noticed. The sample was also stored independently at 30° C. and at 40° C. After 90 days of storage at 30° C., the measured viscosity at room temperature (25° C.±2°) employing a number 3 spindle was 88 cP. After 90 days of storage at 40° C., the measured viscosity at room temperature (25° C.±2°) employing a number 3 spindle was also 88 cP. No change in appearance was noticed in either case.

Example D

Water (74.5 g) was placed in a sanitized mixing vessel. EDTA disodium salt (0.1 g) was added and dissolved into the water with continued mixing. The mixture was cooled and maintained at a temperature of 5 to 8° C. Pluracare F 127 (analogous material to Poloxamer 407, 10 g) was slowly added to avoid introduction of excess air. PVP-iodine (9.73 g) was very slowly added to the mixture with mixing carried out as to avoid entrapment of air. PVP-I % was calculated according to "Available Iodine AS IS" assay found on COA (11.31%) for a total of 1.1% Iodine. Citric acid (50% aqueous solution, 0.2 g) was added with continued mixing. Once the citric acid was dissolved, trisodium citrate dehydrate (25% aqueous solution, 1 g) was added with continued mixing. The remaining ingredients (Floraesters K=20 W jojoba (2.6 g), Laureth-4 (2 g), benzalkonium chloride (0.01 g), and sodium iodide (0.5 g) were independently added to ensure that each ingredient was dissolved before the addition of the next. The batch was mixed with warming to 25° C. until the batch was completely homogeneous. NaOH (0.5 g of 20% by weight aqueous solution) was added and mixed, providing a pH for the mixture in the range of 4.0 to 4.5.
APPEARANCE: Semi-viscous clear liquid
COLOR: Dark reddish/brown
ODOR: Characteristic-iodine
Initial pH @ 25° C.: 4.10
Initial VISCOSITY @ 25° C.: RVT: 74 cP; Spindle 3, 50 RPM
MICROBIOLOGY: <10 CFU/gram, No pathogens The viscosity was evaluated in a Brookfield Viscometer, Model No. RVDVE 11S at room temperature (25° C.±2°) employing a number 3 spindle. The sample was evaluated at 50 rpm) and viscosity, pH and appearance were noted. The viscosity was determined initially (typically within 12 hours of the sample's preparation) and each week thereafter for 90 days. After 90 days, the viscosity was 80 cP at room temperature (25° C.±2°) employing a number 3 spindle, and the pH was 3.79. No change in appearance was noticed. The sample was also stored independently first at room temperature for 6 days and a further 84 days at 30°. After 90 days of storage, the measured viscosity at room temperature (25° C.±2°) employing a number 3 spindle was 58 cP and the pH was 3.57. Additionally, the same initial sample was stored independently first at room temperature for 6 days and a further 84 days at 40° C. After 90 days of storage, the measured viscosity at room temperature (25° C.±2°) employing a number 3 spindle was 54 cP and the pH was 3.02. No change in appearance was noticed in either case.

When any variable occurs more than one time in any constituent or in any formula, its definition in each occurrence is independent of its definition at every other occurrence. Combinations of substituents and/or variables are permissible only if such combinations result in stable compositions.

It is believed the chemical formulas, abbreviations, and names used herein correctly and accurately reflect the underlying compounds reagents and/or moieties. However, the nature and value of the present invention does not depend upon the theoretical correctness of these formulae, in whole or in part. Thus it is understood that the formulas used herein, as well as the chemical names and/or abbreviations attributed to the correspondingly indicated compounds, are not intended to limit the invention in any way, including restricting it to any specific form or to any specific isomer.

When ranges are used herein for physical properties, such as molecular weight, or chemical properties, such as chemical formulae, all combinations and subcombinations of ranges and specific embodiments therein are intended to be included.

The disclosures of each patent, patent application and publication cited or described in this document are hereby incorporated herein by reference, in their entirety.

The invention illustratively disclosed herein suitably may be practiced in the absence of any element which is not specifically disclosed herein. The invention illustratively disclosed herein suitably may also be practiced in the absence of any element which is not specifically disclosed herein and that does not materially affect the basic and novel characteristics of the claimed invention.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

[Embodiment 1] A topical antimicrobial composition comprising:
    a first antimicrobial agent selected from the group consisting of $I_2$, an iodophor, and a combination thereof, wherein the antimicrobial agent is present in an amount sufficient to provide an available iodine concentration of from about 0.25 wt-% or more to about 1.5 wt-% or less;
    a second antimicrobial agent;
    a thickening agent comprising a nonionic cellulose derivative or nonionic copolymer, or combination thereof; and
    water;
    wherein:
        said composition is substantially free of any hydroxycarboxylic acid buffer; and
        said composition is substantially free of any fragrance.

[Embodiment 2] An antimicrobial composition according to Embodiment 1, wherein the first antimicrobial agent comprises an iodophor in an amount of greater than 5 wt-% and sufficient to provide an available iodine concentration of about 1.5 wt-% or less, wherein the iodophor comprises a carrier selected from the group consisting of a polyvinylpyrrolidone, a copolymer of N-vinyl lactam, a polyether glycol, a polyvinyl alcohol, a polyacrylamide, a polysaccharide, and combinations thereof.

[Embodiment 3] An antimicrobial composition according to Embodiment 1 or 2, wherein the composition is substantive to mucosal or skin tissue.

[Embodiment 4] An antimicrobial composition according to any one of Embodiments 1 to 3, wherein the composition has a Brookfield viscosity of about 500 cP or less.

[Embodiment 5] An antimicrobial composition according to Embodiment 4, wherein the composition has a Brookfield viscosity of about 400 cP or less.

[Embodiment 6] An antimicrobial composition according to Embodiment 5, wherein the composition has a Brookfield viscosity of about 300 cP or less.

[Embodiment 7] An antimicrobial composition according to any one of Embodiments 1 to 6, wherein the iodophor carrier comprises povidone.

[Embodiment 8] An antimicrobial composition according to any one of Embodiments 1 to 7, wherein the iodophor comprises povidone-iodine.

[Embodiment 9] An antimicrobial composition according to Embodiment 8, wherein the iodophor comprises povidone-iodine USP.

[Embodiment 10] An antimicrobial composition according to any one of Embodiments 1 to 9, wherein the iodophor further comprises an iodide salt.

[Embodiment 11] An antimicrobial composition according to any one of Embodiments 1 to 10, further comprising a surfactant.

[Embodiment 12] An antimicrobial composition according to Embodiment 11, wherein the surfactant comprises a nonionic or anionic surfactant, or combination thereof.

[Embodiment 13] An antimicrobial composition according to Embodiment 12, wherein the surfactant comprises a nonionic surfactant.

[Embodiment 14] An antimicrobial composition according to Embodiment 13, wherein the surfactant further comprises an anionic surfactant.

[Embodiment 15] An antimicrobial composition according to Embodiment 12 or 14, wherein the anionic surfactant comprises a salt of a fatty acid.

[Embodiment 16] An antimicrobial composition according to any one of Embodiments 1 to 14, wherein the second antimicrobial agent comprises a neutral or cationic antimicrobial agent.

[Embodiment 17] An antimicrobial composition according to Embodiment 16, wherein the second antimicrobial agent comprises a compound selected from the group consisting of: diazolidinyl urea, methylchloroisothiazolinone, methylisothiazolinone, disodium EDTA, and a benzalkonium salt, or a combination thereof.

[Embodiment 18] An antimicrobial composition according to Embodiment 17, wherein the second antimicrobial agent comprises a compound selected from the group consisting of: disodium EDTA and a benzalkonium salt, or a combination thereof.

[Embodiment 19] An antimicrobial composition according to Embodiment 18, wherein the second antimicrobial agent comprises disodium EDTA.

[Embodiment 20] An antimicrobial composition according to any one of Embodiments 1 to 16, wherein the second antimicrobial agent comprises a benzalkonium compound.

[Embodiment 21] An antimicrobial composition according to Embodiment 20, wherein the benzalkonium compound comprises benzalkonium chloride.

[Embodiment 22] An antimicrobial composition according to any one of Embodiments 1 to 20, further comprising a nonionic surfactant.

[Embodiment 23] An antimicrobial composition according to any one of Embodiments 1 to 23, further comprising an emollient.

[Embodiment 24] An antimicrobial composition according to Embodiment 23, wherein the emollient comprises at least one jojoba ester or derivative thereof.

[Embodiment 25] An antimicrobial composition according to Embodiment 23, wherein the emollient comprises a fatty alcohol.

[Embodiment 26] A topical antimicrobial composition according to any one of Embodiments 1 to 25, wherein the thickening agent comprises a nonionic cellulose derivative.

[Embodiment 27] A topical antimicrobial composition according to any one of Embodiments 1 to 26, wherein the nonionic cellulose derivative comprises hydroxyethyl cellulose.

[Embodiment 28] A topical antimicrobial composition according to any one of Embodiments 1 to 25, wherein the thickening agent comprises a nonionic copolymer.

[Embodiment 29] An antimicrobial composition according to any one of Embodiments 1 to 25 and 27, wherein the nonionic copolymer comprises hydrophilic and hydrophobic regions.

[Embodiment 30] A topical antimicrobial composition according to Embodiment 29, wherein the nonionic copolymer comprises a poloxamer.

[Embodiment 31] An antimicrobial composition according to Embodiment 30, wherein the poloxamer has the formula I:

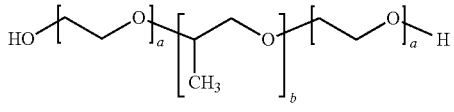

wherein, on average, each a is independently from about 80 to about 120 and b is from about 50 to about 80.

[Embodiment 32] An antimicrobial composition according to Embodiment 31 each a is independently from about 90 to about 110 and b is from about 55 to about 70.

[Embodiment 33] An antimicrobial composition according to any one of Embodiments 30 to 32, wherein the poloxamer has an approximate molecular mass of the poly(oxypropylene) core of 3500 to about 4500 g/mol and about 65 to about 75% of poly(oxyethylene) content by weight of the poloxamer.

[Embodiment 34] An antimicrobial composition according to Embodiment 18, wherein:
the second antimicrobial agent comprises benzalkonium chloride and disodium EDTA;
the surfactant comprises laureth-4; and
the emollient comprises a saponified ester of jojoba oil.

[Embodiment 35] A topical antimicrobial composition comprising:
a first antimicrobial agent selected from the group consisting of $I_2$, an iodophor, and a combination thereof, wherein the antimicrobial agent is present in an amount sufficient to provide an available iodine concentration of from about 0.25 wt-% or more to about 1.5 wt-% or less;
a second antimicrobial agent comprising EDTA or a benzalkonium salt or combination thereof;
a thickening agent comprising a nonionic cellulose derivative or nonionic copolymer, or combination thereof;
an emollient comprising a saponified ester of a fatty acid and fatty alcohol;
a nonionic surfactant comprising laureth-4;

an iodide salt;
and
water;
 wherein:
  said composition is substantially free of any hydroxycarboxylic acid buffer; and
  said composition is substantially free of any fragrance.

[Embodiment 36] A topical antimicrobial composition according to Embodiment 35 comprising:
 a first antimicrobial agent selected from the group consisting of $I_2$, an iodophor, and a combination thereof, wherein the antimicrobial agent is present in an amount sufficient to provide an available iodine concentration of from about 0.25 wt-% or more to about 1.5 wt-% or less;
 a second antimicrobial agent comprising EDTA and a benzalkonium salt;
 a thickening agent comprising a nonionic copolymer;
 an emollient comprising a saponified ester of a fatty acid and fatty alcohol;
 a nonionic surfactant comprising laureth-4;
 an iodide salt;
 and
 water;
  wherein:
   said composition is substantially free of any hydroxycarboxylic acid buffer; and
 said composition is substantially free of any fragrance.

[Embodiment 37] A topical antimicrobial composition according to Embodiment 35 comprising:
 a first antimicrobial agent selected from the group consisting of $I_2$, an iodophor, and a combination thereof, wherein the antimicrobial agent is present in an amount sufficient to provide an available iodine concentration of from about 0.25 wt-% or more to about 1.5 wt-% or less;
 a second antimicrobial agent comprising EDTA and a benzalkonium salt or combination thereof;
 a thickening agent comprising a nonionic cellulose derivative;
 an emollient comprising a saponified ester of a fatty acid and fatty alcohol;
 a nonionic surfactant comprising laureth-4;
 an iodide salt;
 and
 water;
  wherein:
   said composition is substantially free of any hydroxycarboxylic acid buffer; and
   said composition is substantially free of any fragrance.

[Embodiment 38] A topical antimicrobial composition according to Embodiment 36 wherein the nonionic copolymer is a poloxamer.

[Embodiment 39] A method of disinfecting tissue comprising:
 applying directly to tissue an antiseptic composition at use concentration, wherein the use concentration of the composition comprises:
  an antimicrobial composition according to any one of Embodiments 1 to 34; and
  water; and
 allowing the antiseptic composition to remain on the tissue;
 wherein the composition has a pH of 1.5 to 6.5.

[Embodiment 40] A method of making an antiseptic composition at use concentration, the method comprising combining components comprising:
 an iodophor comprising a carrier selected from the group consisting of a polyvinylpyrrolidone, a copolymer of N-vinyl lactam, a polyether glycol, a polyvinyl alcohol, a polyacrylamide, a polysaccharide, and combinations thereof; wherein the iodophor is present in an amount sufficient to provide an available iodine concentration of at least 0.25 wt-%;
 a second antimicrobial agent;
 a thickening agent comprising a nonionic cellulose derivative or nonionic copolymer, or combination thereof; and
 water;
  wherein:
   said composition is substantially free of any hydroxycarboxylic acid buffer;
   said antiseptic composition at use concentration is an antimicrobial composition according to any one of Embodiments 1 to 34; and
   said composition is substantially free of any fragrance;
 for a time and under conditions effective to form the antiseptic composition at use concentration.

[Embodiment 41] A method of disinfecting skin of a subject comprising:
 prior to an invasive procedure, applying directly to the skin of the subject an antiseptic composition at use concentration, wherein the use concentration of the composition comprises:
  an antimicrobial composition according to any one of Embodiments 1 to 34; and
 allowing the antiseptic composition to remain on the skin during the invasive procedure.

[Embodiment 42] A method of Embodiment 41, wherein the invasive procedure is a surgical, catheterization, or needle puncture procedure.

[Embodiment 43] A method of disinfecting mucosal tissue of a subject comprising:
 applying directly to the mucosal tissue of the subject an antiseptic composition at use concentration, wherein the use concentration of the composition comprises:
  an antimicrobial composition according to any one of Embodiments 1 to 34; and
 allowing the antiseptic composition to remain on the mucosal tissue.

[Embodiment 44] A method of Embodiment 43, wherein the mucosal tissue is nasal tissue.

[Embodiment 45] A method of decolonizing the nasal passages of a subject, the method comprising: applying an antimicrobial composition according to any one of Embodiments 1 to 34 to the nasal passages of the subject.

[Embodiment 46] A method of disinfecting the tissue of a subject, the method comprising: applying an antimicrobial composition according to any one of Embodiments 1 to 34 to the tissue of the subject.

What is claimed:

1. A method of disinfecting skin of a subject comprising: prior to an invasive procedure,
 applying directly to the skin of the subject an antiseptic composition comprising:
  a first antimicrobial agent selected from the group consisting of $I_2$, an iodophor, and a combination thereof, wherein the antimicrobial agent is present in an amount sufficient to provide an available iodine concentration of from about 0.25 wt-% or more to about 1.5 wt-% or less;
a second antimicrobial agent;
a nonionic or anionic surfactant;
a thickening agent comprising a nonionic cellulose derivative or nonionic copolymer, or combination thereof; and
water;
wherein:
said composition is free of any hydroxycarboxylic acid buffer and any fragrance; and
maintaining the antiseptic composition's contact on the skin during the procedure.

2. The method of claim 1, wherein the invasive procedure is a surgical, catheterization, or needle puncture procedure.

3. The method of claim 1 wherein the antiseptic composition comprises a nonionic surfactant.

4. The method of claim 1, wherein the antiseptic composition has a Brookfield viscosity of about 500 cP or less.

5. The method of claim 1, wherein the iodophor comprises povidone.

6. The method of claim 1, wherein the iodophor comprises povidone-iodine.

7. The method of claim 1, wherein the antiseptic composition comprises an anionic surfactant.

8. The method of claim 1, wherein the antiseptic composition further comprises an emollient comprising a fatty alcohol.

9. The method of claim 1, wherein the thickening agent is a poloxamer having the formula I:

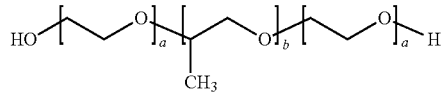

wherein, on average, each a is independently from about 80 to about 120 and b is from about 50 to about 80.

10. The method of claim 1, wherein the antiseptic composition further comprises an emollient comprising at least one jojoba ester or derivative thereof.

11. The method of 1, wherein the second antimicrobial agent is selected from the group consisting of: diazolidinyl urea, methylchloroisothiazolinone, methylisothiazolinone, disodium EDTA, a benzalkonium salt, and any combination thereof.

12. The method of claim 1, wherein the iodophore is povidone iodine, the second antimicrobial agent comprises benzalkonium salt and EDTA, the nonionic surfactant is laureth-4, and the nonionic copolymer is a poloxamer, wherein the antiseptic composition further comprises an emollient comprising at least one jojoba ester or derivative thereof.

13. The method of claim 12, wherein the antiseptic composition comprises about 5 wt % to about 16 wt % of the povidone iodine, about 0.005 wt % to about 0.3 wt % of the benzalkonium salt, about 0.05 wt % to about 0.3 wt % of the EDTA, about 0.5 wt % to about 7 wt % of the laureth-4, about 2 wt % to about 12 wt % of the poloxamer, about 1 wt % to about 8 wt % of the jojoba ester,
wherein antiseptic composition further comprises sodium iodide and sodium hydroxide.

14. The method according to claim 1, wherein the nonionic copolymer comprises hydrophilic and hydrophobic regions.

15. The method according to claim 1, wherein the nonionic copolymer comprises a poloxamer.

16. A method of disinfecting skin of a subject comprising:
applying an antiseptic composition directly to a subject's skin, the composition comprising:
a first antimicrobial agent selected from the group consisting of $I_2$, an iodophor, and any combination thereof, wherein the antimicrobial agent is present in an amount sufficient to provide an available iodine concentration of from about 0.25 wt-% to about 1.5 wt-%;
a second antimicrobial agent;
a surfactant;
a thickening agent comprising a nonionic cellulose derivative or nonionic copolymer, or any combination thereof; and
water;
wherein the composition has only a de minimis amount hydroxycarboxylic acid buffer and a de minimis amount of fragrance.

17. A method of disinfecting skin of a subject comprising:
applying an antiseptic composition directly to a subject's skin, the composition consisting essentially of:
a first antimicrobial agent selected from the group consisting of $I_2$, an iodophor, and any combination thereof, wherein the antimicrobial agent is present in an amount sufficient to provide an available iodine concentration of from about 0.25 wt-% to about 1.5 wt-%;
a second antimicrobial agent;
a surfactant;
a thickening agent comprising a nonionic cellulose derivative or nonionic copolymer, or any combination thereof; and
water;
wherein the composition has only a de minimis amount hydroxycarboxylic acid buffer and a de minimis amount of fragrance.

* * * * *